US00PP24011P3

(12) United States Plant Patent
Egger

(10) Patent No.: US PP24,011 P3
(45) Date of Patent: Oct. 29, 2013

(54) ***KNIPHOFIA* PLANT NAMED 'LEMON POPSICLE'**

(50) Latin Name: ***Kniphofia* spp.**
Varietal Denomination: Lemon Popsicle

(75) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 81 days.

(21) Appl. No.: 13/385,799

(22) Filed: Mar. 6, 2012

(65) Prior Publication Data

US 2013/0239281 P1 Sep. 12, 2013

(51) Int. Cl.
*A01H 5/00* (2006.01)

(52) U.S. Cl.
USPC ..... Plt./443

(58) Field of Classification Search
USPC ..... Plt./443
See application file for complete search history.

*Primary Examiner* — Susan McCormick Ewoldt
(74) *Attorney, Agent, or Firm* — Klarquist Sparkman, LLP

(57) ABSTRACT

A new and distinct *Kniphofia* plant characterized by numerous spikes of yellow flowers the first year, repeat blooming from June through September in Canby, Oreg., a compact habit with multiple crowns, narrow, grassy leaves, and excellent vigor.

1 Drawing Sheet

Botanical denomination: *Kniphofia* spp.
Cultivar designation: 'Lemon Popsicle'.

BACKGROUND OF THE INVENTION

The present invention relates to a new and distinct *Kniphofia*, and given the cultivar name is 'Lemon Popsicle'. *Kniphofia* is in the family Asphodelaceae. 'Lemon Popsicle' is a hybrid resulting from a planned breeding program to produce a series of compact, reblooming *Kniphofia*. The cross was made using the following proprietary, unreleased plants: *Kniphofia* 8-1, as the seed parent, and *Kniphofia* 9-1, as the pollen parent. It was selected for best habit, flower color, reblooming, and crown count from many seedlings of the cross in Canby, Oreg.

Compared to the seed parent, *Kniphofia* 8-1, the new cultivar has yellow rather than bicolor yellow and orange flowers.

Compared to the pollen parent, *Kniphofia* 9-1, the new cultivar has shorter flower stalks that are more free flowering.

Compared to *Kniphofia* 'Little Maid' (an unpatented plant), the new cultivar is more vigorous and has clear deep yellow flowers rather than bicolor light yellow and cream flowers.

Compared to *Kniphofia* 'Dwarf Yellow' (an unpatented plant), the new cultivar is a deeper yellow color and more free flowering.

SUMMARY OF THE INVENTION

The new cultivar is unique and characterized by:

1. numerous spikes of yellow flowers the first year
2. repeat blooming from June through September in Canby, Oreg.
3. compact habit with multiple crowns
4. narrow, grassy leaves
5. excellent vigor, fills a one gallon pot the first year from tissue culture This new cultivar has been reproduced only by asexual propagation (division, tissue culture). Each of the progeny exhibits identical characteristics to the new cultivar. Asexual propagation by leaf cuttings, tissue culture, and division using standard techniques as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a plant of a one-year-old *Kniphofia* 'Lemon Popsicle' in the ground in the garden in July in Canby, Oreg.

DETAILED PLANT DESCRIPTION

The following is a detailed description of the new *Kniphofia* cultivar based on observations of one and a half year old specimens growing in the ground outside in full sun in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The *Royal Horticultural Society Colour Chart*, 5$^{th}$ edition, published 2007.

Plant:

*Type*.—Rhizomatous herbaceous perennial.
*Hardiness*.—USDA Zones 6 to 9.
*Size*.—Grows to 45 cm wide and 45 cm tall from the top of the soil to the top of the foliage, grows to 65 cm tall to the top of the inflorescence.
*Average number of leaves*.—50.
*Form*.—Clumping.

Leaf:

*Type*.—Simple.
*Shape*.—Strap-like.

*Arrangement*.—Basal rosette.
*Blade size*.—Grows to 50 cm long and 18 mm wide.
*Margins*.—Minutely serrulate.
*Apex*.—Acuminate.
*Base*.—Clasping.
*Surface texture*.—Glabrous on both surfaces.
*Venation*.—Parallel.
*Color*.—Top and bottom side Green 137A.

Inflorescence:
*Type*.—Spike-like scapose raceme.
*Number of flowers per raceme*.—About 90.
*Inflorescence*.—Grows to 20 cm long and 4.4 cm wide.
*Peduncle description*.—Grows to 45 cm long and 7 mm wide, glabrous, Yellow Green 146B.
*Pedicle description*.—2.5 mm long, glabrous, Yellow Green 146C.
*Bloom time*.—Late June through September in Canby, Oreg.
*Lastingness*.—An inflorescence lasts for 2 to 4 weeks depending on the temperatures.

Flower bud:
*Size*.—22 mm long and 5 mm wide.
*Shape*.—Cylindrical.
*Surface texture*.—Glabrous.
*Color*.—Yellow 10B with tints of Green Yellow 1C near base and on veins.

Flower:
*Type*.—Actinomorphic.
*Shape*.—Cylindrical and tubular.
*Size*.—Grows to 2.8 cm deep and 10 mm wide.
*Texture*.—Waxy.
*Surface texture*.—Glabrous inside and outside.
*Color*.—Inside and outside, Yellow 5C darkening to 9C with veins Green Yellow 1C.
*Corolla description*.—6 lobed fused tepals, 22 mm long and 11 mm wide, each lobe 3 mm wide and 4 mm long, ovate to oblong, margin entire, tip notched; glabrous inside and out.
*Pistil description*.—One, 27 mm long, ovary 4 mm long 2.5 mm wide, Yellow Green 144A, style extruding, 18 mm long, stigma and style Green Yellow 1C.
*Stamen*.—6, 31 mm long, filaments 30 mm long, and Green Yellow 1C, anthers 1.5 mm long and Yellow Orange 20A, pollen none.
*Fragrance*.—None.

Fruit and seed: Few capsules seen, 5 mm long and 4 mm wide, glabrous, subglobous, Green 137A.

Pest and diseases: No known resistances to pests or diseases. No problems have been observed on this plant grown under commercial conditions in Canby, Oreg.

I claim:

1. A new and distinct *Kniphofia* plant as herein shown and described.

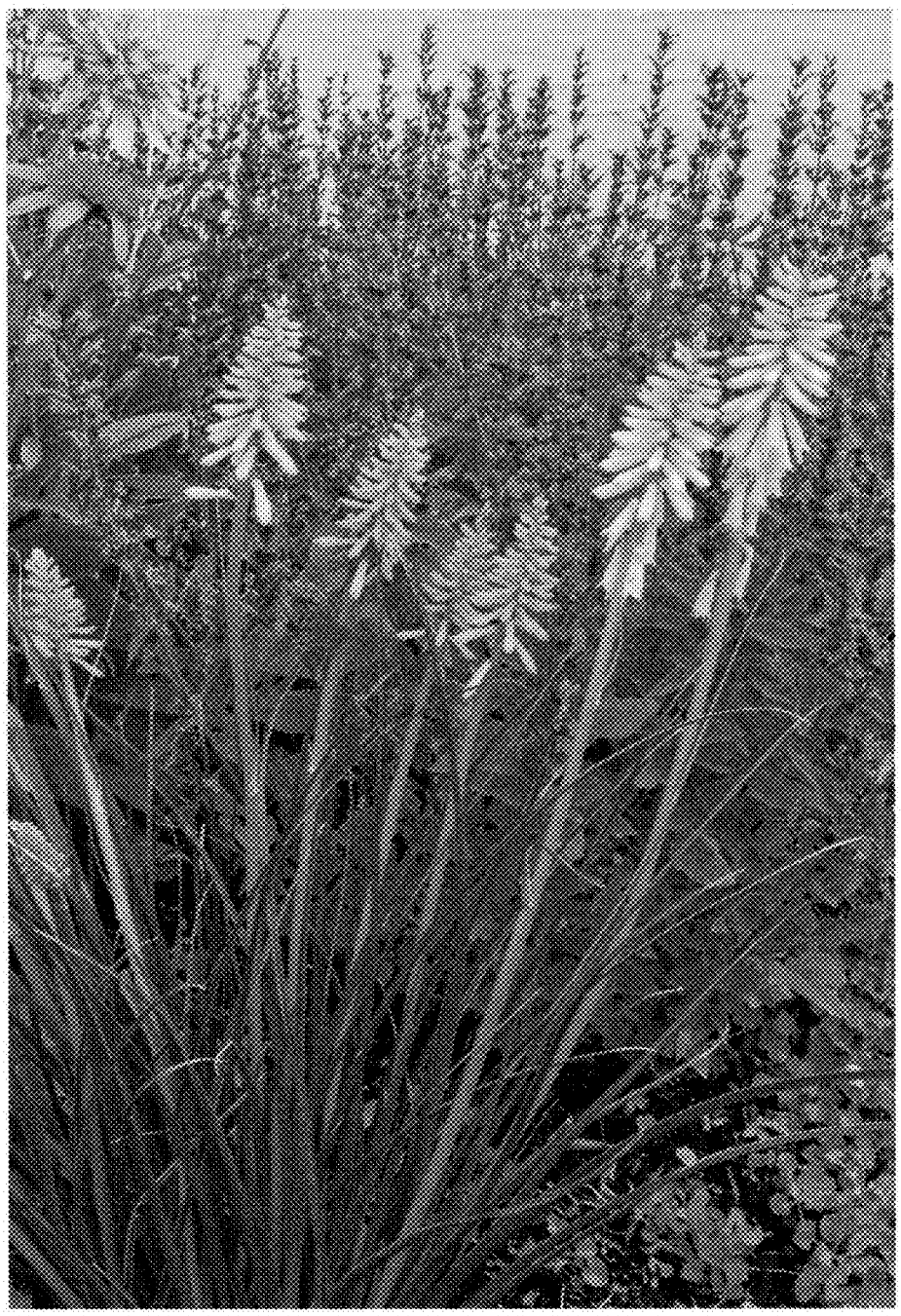

* * * * *